(12) United States Patent
Mak

(10) Patent No.: US 11,377,727 B2
(45) Date of Patent: Jul. 5, 2022

(54) METHOD FOR PREPARING BACTERICIDAL FILM ON FIBER CLOTH

(71) Applicant: Fook Chi Mak, Hong Kong (CN)

(72) Inventor: Fook Chi Mak, Hong Kong (CN)

( * ) Notice: Subject to any disclaimer, the term of this patent is extended or adjusted under 35 U.S.C. 154(b) by 0 days.

(21) Appl. No.: 17/106,428

(22) Filed: Nov. 30, 2020

(65) Prior Publication Data

US 2021/0388485 A1 Dec. 16, 2021

(51) Int. Cl.
| | | |
|---|---|---|
| *C23C 14/34* | (2006.01) |
| *A01N 59/00* | (2006.01) |
| *A01N 59/16* | (2006.01) |
| *A61L 2/238* | (2006.01) |
| *C23C 14/02* | (2006.01) |
| *C23C 14/06* | (2006.01) |
| *C23C 14/14* | (2006.01) |
| *D06M 11/73* | (2006.01) |
| *D06M 11/77* | (2006.01) |
| *D06M 11/83* | (2006.01) |
| *A61L 101/02* | (2006.01) |
| *A61L 101/12* | (2006.01) |

(52) U.S. Cl.
CPC .......... *C23C 14/3464* (2013.01); *A01N 59/00* (2013.01); *A01N 59/16* (2013.01); *A61L 2/238* (2013.01); *C23C 14/02* (2013.01); *C23C 14/0635* (2013.01); *C23C 14/14* (2013.01); *D06M 11/73* (2013.01); *D06M 11/77* (2013.01); *D06M 11/83* (2013.01); *A61L 2101/02* (2020.08); *A61L 2101/12* (2020.08); *A61L 2202/26* (2013.01)

(58) Field of Classification Search
CPC . C23C 14/3464; C23C 41/02; C23C 14/0635; C23C 14/14; A01N 59/00; A01N 59/16; A61L 2/238; A61L 2101/02; A61L 2101/12; A61L 2202/26; D06M 11/73; D06M 11/77; D06M 11/83
See application file for complete search history.

(56) References Cited

U.S. PATENT DOCUMENTS

| 5,631,498 A | * | 5/1997 | Anschel | ............. | H01L 21/4846 |
| | | | | | 257/690 |
| 2007/0128826 A1 | * | 6/2007 | Chen | .................. | H01L 21/0237 |
| | | | | | 438/455 |
| 2009/0197494 A1 | * | 8/2009 | Chang | .................. | C23C 14/205 |
| | | | | | 204/192.15 |

FOREIGN PATENT DOCUMENTS

| CN | 101080144 A | * | 11/2007 | | |
| CN | 102179970 A | * | 9/2011 | | |
| CN | 104944798 A | * | 9/2015 | | |
| CN | 109267023 A | * | 1/2019 | ............. | A01N 25/08 |
| CN | 109485271 A | * | 3/2019 | | |
| CN | 109704597 A | * | 5/2019 | | |
| CN | 110184572 A | * | 8/2019 | .......... | C03C 17/002 |
| CN | 210143880 U | * | 3/2020 | | |
| CN | 111636198 A | * | 9/2020 | | |

OTHER PUBLICATIONS

CN-111636198-A Translation (Year: 2020).*
CN-102179970-A Translation (Year: 2011).*
CN-109485271-A Translation (Year: 2019).*
CN-104944798-A Translation (Year: 2015).*
CN-101080144-A Translation (Year: 2007).*

* cited by examiner

*Primary Examiner* — Jennifer Wecker
*Assistant Examiner* — Patrick S Ott

(57) ABSTRACT

A method for preparing a bactericidal film on fiber cloth, comprising cleansing a reel of fiber cloth; placing the reel of fiber cloth into a vacuum chamber; supplying a DC power and a mid-frequency power; introducing argon gas to increase the chamber pressure to 0.3 Pa; position sputtering targets in the following order: silicon target, silicon carbide target, silver target, silicon carbide target, silver target, silicon carbide target and silver target, and then sputtering the targets simultaneously; wherein the silicon targets act as a bonding layer between the bactericidal film and the substrate; stopping the silicon targets, the silicon carbide targets and the silver targets first, and then turning off the argon gas; injecting air into the chamber until the pressure in the chamber and the atmospheric pressure are balanced.

3 Claims, No Drawings

METHOD FOR PREPARING BACTERICIDAL FILM ON FIBER CLOTH

TECHNICAL FIELD

This invention y relates to the technical field of composite material vacuum coating, and more particularly, to a method for preparing a bactericidal film on fiber cloth.

BACKGROUND

With the social development and technological progress, production level has been significantly improved and new technologies have been extensively applied to all aspect of life. As living standards generally increase worldwide, people are demanding higher performance of materials. Fiber cloth is a common material used widely in various fields especially in medical protection, which normally serves as a disposable material for making protection articles such as masks. However, despite its wide range of use, the function of conventional fiber cloth is limited. For instance, conventional fiber cloth fails to prevent bacterial growth. As a result, if the conventional cloth products need to be reused, they must be sterilized with special equipment, resulting in inconvenience and waste of resource.

SUMMARY

The purpose of the present invention is to provide a method for preparing a bactericidal film on fiber cloth, which effectively solves technical problems of the conventional fiber cloth which is limited in function, wastes resource and is not sanitary and eco-friendly.

To achieve the above purpose, the present disclosure adopts the following technical solution: a method for preparing a bactericidal film on fiber cloth, comprising the steps of:

(1) Preprocessing: cleansing a reel of fiber cloth and blow-drying at a low temperature;

(2) Vacuum processing: placing the reel of fiber cloth into a vacuum chamber, and vacuuming the chamber to $1 \times 10^{-3}$ Pa;

(3) Coating a bactericidal film layer: switching-on a DC power supply and a mid-frequency power supply, then regulating the voltage to 600-1000V and 30-40V respectively, wherein the duty ratio is 20-30%; introducing argon gas, thereby enabling the vacuum chamber to reach 0.3 Pa; initiating silicon sputtering targets, silicon carbide sputtering targets and silver sputtering targets; subsequently, initiating the reel of fiber cloth, wherein the advancing linear speed of the fiber cloth is 0.1-0.3 m/s, the current density of the silicon and silicon carbide sputtering targets are 4-6 A, and the current density of the silver sputtering target is 0.3-0.6 A; regulating the chamber temperature to 10-20° C.; according to the advancing direction of the fiber cloth, arranging the sputtering targets in the following sequence: silicon target, silicon carbide target, silver target, silicon carbide target, silver target, silicon carbide target and silver target, and then making them sputter simultaneously, thus forming a multi-layer of bactericidal film layer of silicon carbide and silver on the surface of the fiber cloth; while the silicon targets act as a bonding layer between the bactericidal film and the substrate.

(4) Completing the film coating: stopping the reel of fiber cloth first, then stopping the silicon targets, the silicon carbide targets and the silver targets, and then turning off the argon gas; letting the chamber cool after waiting for 5-10 minutes; subsequently, injecting air into the chamber intermittently until the pressure in the chamber and the atmospheric pressure are balanced; finally, taking out the reel of fiber cloth, thereby completing the whole coating process.

In another aspect of the present disclosure, in step (1), the reel of fiber cloth is cleaned by absorbing and removing the dust and gas off the cloth surface, and the blow-drying temperature does not exceed a temperature of 60° C.

In another aspect of the present disclosure, in step (2), the flow rate of argon gas is 100-250 sccm, and the coating duration is 10-60 seconds.

Through adopting the techniques of the present disclosure, the entire process does not need chemical processing, and the coated film layer will not damage the surface of the fiber cloth. The bactericidal film layer is formed by using silicon carbide targets and silver targets. The large number of carbon atoms contained in the fiber and the bonding layer silicon atoms have good binding force. The silver sputtering targets are initiated to enable nano silver particles with bactericidal effect to be uniformly distributed on the fiber cloth, thereby forming a bactericidal film with bactericidal effect. Additionally, during the coating process, the fiber cloth advances at a constant speed, which allows the sputtered film on fiber cloth to be more uniform and also prevents the fiber cloth from being damaged by local high temperature. The entire process reduces health risk and is eco-friendly. The present disclosure maintains the appearance and various properties of fiber cloth, achieves an ideal bactericidal effect, and provides convenient preparation and low investment cost of equipment, and has a wide application range.

DETAILED DESCRIPTION

Detailed embodiments are combined hereinafter to clearly and completely describe the techniques of the present disclosure. Obviously, the described embodiments are merely a representative part but not all of the embodiments of the present invention. The specification of the present invention allows those skilled in the art to obtain other embodiments without paying creative labor, and thus all of which shall fall into the scope of the present disclosure.

A method for preparing a bactericidal film on fiber cloth, comprising the steps of:

(1) Preprocessing: cleansing a reel of fiber cloth and blow-drying at a low temperature; the fiber cloth may be cleansed in various ways; through the cleansing, the surface of the fiber cloth is kept clean and dry before coating, which strengthens the binding force of the film layer, and significantly improve the coating quality of the bactericidal film.

(2) Vacuum processing: placing the reel of fiber cloth into a vacuum chamber, and vacuuming the chamber to $1 \times 10^{-3}$ Pa;

(3) Coating a bactericidal film layer: switching-on a mid-frequency power supply and regulating the voltage to 30-40V, wherein the duty ratio is 20-30%; at the same time switching on a DC power supply and regulating the voltage to 600-1000V, introducing argon gas, thereby enabling the vacuum degree to reach 0.3 Pa; initiating silicon carbide targets by the mid-frequency power supply and the silver sputtering targets by the DC power supply; subsequently, initiating the reel of fiber cloth, wherein the advancing linear speed of the fiber cloth is set to 0.1-0.3 m/s, the current density of the silicon carbide sputtering target is 4-6 A, and the current density of the silver sputtering target is 0.3-0.6 A; regulating the chamber temperature to 10-12° C.; in the advancing direction of the fiber cloth, sequentially position the sputtering targets in the following order:

silicon target, silicon carbide target, silver target, silicon carbide target, silver target, silicon carbide target and silver target, and then making them sputter simultaneously, thus forming a multilayered bactericidal film layer of silicon carbide and silver on the surface of the fiber cloth;

(4) Completing the film coating: stopping the reel of fiber cloth first, then stopping the silicon targets, the silicon carbide targets and the silver targets, and then turning off the argon gas; letting the chamber cool after waiting for 5-10 minutes; subsequently, injecting air into the vacuum chamber intermittently until the pressure in the chamber and the atmospheric pressure are balanced; finally, taking out the reel of fiber cloth, thereby completing the entire coating process.

In another aspect of the present disclosure, in step (1), the reel of fiber cloth is cleaned by absorbing and removing the dust and gas off the cloth surface, and the blow-drying temperature does not exceed a temperature of 60° C.

In another aspect of the present disclosure, in step (2), the flow rate of argon gas is 100-250 sccm, and the coating duration is 10-60 seconds.

Embodiment 1

A method for preparing a bactericidal film on fiber cloth, comprising the steps of:
(1) Preprocessing: cleansing a reel of fiber cloth and blow-drying at a low temperature; the fiber cloth may be cleansed in various ways; through the cleansing, the surface of the fiber cloth is kept clean and dry before coating, which may strengthen the binding force of the film layer, and significantly improve the coating quality of the bactericidal film.
(2) Vacuum processing: placing the reel of fiber cloth into a vacuum chamber, and vacuuming the chamber to $1\times10^{-3}$ Pa;
(3) Coating a bactericidal film layer: switching-on a mid-frequency power supply and regulating the voltage to 30V, wherein the duty ratio is 20-30%; at the same time switching on a DC power supply and regulating the voltage to 700V, introducing argon gas, thereby enabling the vacuum degree to reach 0.3 Pa; initiating silicon carbide targets by the mid-frequency power supply and the silver sputtering targets by the DC power supply; subsequently, initiating the reel of fiber cloth, wherein the advancing linear speed of the fiber cloth is set to 0.1-0.3 m/s, the current density of the silicon carbide sputtering target is 6 A, and the current density of the silver sputtering target is 0.4 A; regulating the chamber temperature to 18° C.; in the advancing direction of the fiber cloth, sequentially position the sputtering targets in the following order: silicon target, silicon carbide target, silver target, silicon carbide target, silver target, silicon carbide target and silver target, and then sputtering all the targets simultaneously, thus forming a multilayered bactericidal film layer of silicon carbide and silver on the surface of the fiber cloth;
(4) Completing the film coating: stopping the reel of fiber cloth first, then stopping the silicon targets, the silicon carbide targets and the silver targets, and then turning off the argon gas; letting the chamber cool after waiting for 5 minutes; subsequently, injecting air into the vacuum chamber intermittently until the pressure in the chamber and the atmospheric pressure are balanced; finally, taking out the reel of fiber cloth, thereby completing the whole coating process.

Embodiment 2

A method for preparing a bactericidal film on fiber cloth, comprising the steps of:

(1) Preprocessing: cleansing a reel of fiber cloth and blow-drying at a low temperature; the fiber cloth may be cleansed in various ways; through the cleansing, the surface of the fiber cloth is kept clean and dry before coating, which may strengthen the binding force of the film layer, and significantly improve the coating quality of the bactericidal film.
(2) Vacuum processing: placing the reel of fiber cloth into a vacuum chamber, and vacuuming the chamber to $1\times10^{-3}$ Pa;
(3) Coating a bactericidal film layer: switching-on a mid-frequency power supply and regulating the voltage to 32V, wherein the duty ratio is 32%; at the same time switching on a DC power supply and regulating the voltage to 780V, introducing argon gas, thereby enabling the vacuum degree to reach 0.3 Pa; initiating silicon carbide targets by the mid-frequency power supply and the silver sputtering targets by the DC power supply; subsequently, initiating the reel of fiber cloth, wherein the advancing linear speed of the fiber cloth is regulated to 0.1-0.3 m/s, the current density of the silicon carbide sputtering target is 6 A, and the current density of the silver sputtering target is 0.4 A; regulating the chamber temperature to 16° C.; in the advancing direction of the fiber cloth, sequentially position the sputtering targets in the following sequence: silicon target, silicon carbide target, silver target, silicon carbide target, silver target, silicon carbide target and silver target, and then making them sputter simultaneously, thus forming a multilayered bactericidal film layer of silicon carbide and silver on the surface of the fiber cloth;
(4) Completing the film coating: stopping the reel of fiber cloth first, then stopping the silicon targets, the silicon carbide targets and the silver targets, and then turning off the argon gas; letting the chamber cool after waiting for 6 minutes; subsequently, injecting air into the vacuum chamber intermittently until the pressure in the chamber and the atmospheric pressure are balanced; finally, taking out the reel of fiber cloth, thereby completing the whole coating process.

Embodiment 3

A method for preparing a bactericidal film on fiber cloth, comprising the steps of:
(1) Preprocessing: cleansing a reel of fiber cloth and blow-drying at a low temperature; the fiber cloth may be cleansed in various ways; through the cleansing, the surface of the fiber cloth is kept clean and dry before coating, which may strengthen the binding force of the film layer, and significantly improve the coating quality of the bactericidal film.
(2) Vacuum processing: placing the reel of fiber cloth into a vacuum chamber, and vacuuming the chamber to $1\times10^{-3}$ Pa;
(3) Coating a bactericidal film layer: switching-on a mid-frequency power supply and regulating the voltage to 36V, wherein the duty ratio is 35%; at the same time switching on a DC power supply and regulating the voltage to 850V, introducing argon gas, thereby enabling the vacuum degree to reach 0.3 Pa; initiating silicon carbide targets by the mid-frequency power supply and the silver sputtering targets by the DC power supply; subsequently, initiating the reel of fiber cloth, wherein the advancing linear speed of the fiber cloth is 0.1-0.3 m/s, the current density of the silicon carbide sputtering target is 6 A, and the current density of the silver sputtering target is 0.4 A; regulating the chamber temperature to 15° C.; according to the advancing direction of the fiber cloth, sequentially arranging the sputtering targets in the following sequence: silicon target, silicon carbide target, silver target, silicon carbide target, silver target, silicon carbide target and silver target, and sputtering all targets simultaneously, thus forming a multilayered bactericidal film layer of silicon carbide and silver on the surface of the fiber cloth;

(4) Completing the film coating: stopping the reel of fiber cloth first, then stopping the silicon targets, the silicon carbide targets and the silver targets, and then turning off the argon gas; letting the chamber cool after waiting for 7 minutes; subsequently, injecting air into the vacuum chamber section by section until the pressure in the chamber and the atmospheric pressure are balanced; finally, taking out the reel of fiber cloth, thereby completing the whole coating process.

Embodiment 4

A method for preparing a bactericidal film on fiber cloth, comprising the steps of:
(1) Preprocessing: cleansing a reel of fiber cloth and blow-drying at a low temperature; the fiber cloth may be cleansed in various ways; through the cleansing, the surface of the fiber cloth is kept clean and dry before coating, which may strengthen the binding force of the film layer, and significantly improve the coating quality of the bactericidal film.
(2) Vacuum processing: placing the reel of fiber cloth into a vacuum chamber, and vacuuming the chamber to a vacuum degree of $1\times10^{-3}$ Pa;
(3) Coating a bactericidal film layer: switching-on a mid-frequency power supply and regulating the voltage to 38V, wherein the duty ratio is 37%; at the same time switching on a DC power supply and regulating the voltage to 910V, introducing argon gas, thereby enabling the vacuum degree to reach 0.3 Pa; initiating silicon carbide targets by the mid-frequency power supply and the silver sputtering targets by the DC power supply; subsequently, initiating the reel of fiber cloth, wherein the advancing linear speed of the fiber cloth is 0.1-0.3 m/s, the current density of the silicon carbide sputtering target is 6 A, and the current density of the silver sputtering target is 0.4 A; regulating the chamber temperature to 13° C.; according to the advancing direction of the fiber cloth, sequentially arranging the sputtering targets in the following sequence: silicon target, silicon carbide target, silver target, silicon carbide target, silver target, silicon carbide target and silver target, and then making them sputter simultaneously, thus forming a multilayered bactericidal film layer of silicon carbide and silver on the surface of the fiber cloth;
(4) Completing the film coating: stopping the reel of fiber cloth first, then stopping the silicon targets, the silicon carbide targets and the silver targets, and then turning off the argon gas; letting the chamber cool after waiting for 8 minutes; subsequently, injecting air into the vacuum chamber section by section until the pressure in the chamber and the atmospheric pressure are balanced; finally, taking out the reel of fiber cloth, thereby completing the whole coating process.

Embodiment 5

A method for preparing a bactericidal film on fiber cloth, comprising the steps of:
(1) Preprocessing: cleansing a reel of fiber cloth and blow-drying at a low temperature; the fiber cloth may be cleansed in various ways; through the cleansing, the surface of the fiber cloth is kept clean and dry before coating, which may strengthen the binding force of the film layer, and significantly improve the coating quality of the bactericidal film.
(2) Vacuum processing: placing the reel of fiber cloth into a vacuum chamber, and vacuuming the chamber to a vacuum degree of $1\times10^{-3}$ Pa;
(3) Coating a bactericidal film layer: switching-on a mid-frequency power supply and regulating the voltage to 40V, wherein the duty ratio is 30%; at the same time switching on a DC power supply and regulating the voltage to 1000V, introducing argon gas, thereby enabling the vacuum degree to reach 0.3 Pa; initiating silicon carbide targets by the mid-frequency power supply and the silver sputtering targets by the DC power supply; subsequently, initiating the reel of fiber cloth, wherein the advancing linear speed of the fiber cloth is 0.1-0.3 m/s, the current density of the silicon carbide sputtering target is 6 A, and the current density of the silver sputtering target is 0.4 A; regulating the chamber temperature to 12° C.; according to the advancing direction of the fiber cloth, sequentially arranging the sputtering targets in the following sequence: silicon target, silicon carbide target, silver target, silicon carbide target, silver target, silicon carbide target and silver target, and then making them sputter simultaneously, thus forming a multilayered bactericidal film layer of silicon carbide and silver on the surface of the fiber cloth;
(4) Completing the film coating: stopping the reel of fiber cloth first, then stopping the silicon targets, the silicon carbide targets and the silver targets, and then turning off the argon gas; letting the chamber cool after waiting for 10 minutes; subsequently, injecting air into the vacuum chamber section by section until the pressure in the chamber and the atmospheric pressure are balanced; finally, taking out the reel of fiber cloth, thereby completing the whole coating process.

Embodiment 6

After respectively measuring the film layer binding force of the bactericidal film on each of the fiber clothes obtained from the aforesaid embodiments 1-5, the measurement results are shown in the following table:

| Embodiment | 1 | 2 | 3 | 4 | 5 |
|---|---|---|---|---|---|
| Binding Force (N) | 60.5 | 62 | 63.5 | 65 | 67 |

From the above results, it can be seen that, the film layer binding force of the bactericidal film on each of the fiber clothes obtained through adopting the techniques of the present disclosure is greater than 60N, which indicates that the film layer binding force is strong enough to meet the requirements of ordinary fiber cloth products.

Embodiment 7

The fiber clothes obtained from embodiments 1-5 are all protective masks made of the same material, which are respectively numbered as groups 1-5, and a conventional protective mask made of the same material is taken as a control group. The number of bacterial colonies on the surface of the six groups of samples is respectively observed after 5, 10 and 24 hours under the same using condition. The results are shown in the following table:

| Samples | Group 1 | Group 2 | Group 3 | Group 4 | Group 5 | Control Group |
|---|---|---|---|---|---|---|
| 5 hours (number/cm$^2$) | 9 | 11 | 14 | 10 | 7 | 45 |
| 10 hours (number/cm$^2$) | 4 | 5 | 6 | 4 | 3 | 56 |
| 24 hours (number/cm$^2$) | 0 | 0 | 0 | 0 | 0 | 72 |

Based on the above results, the bactericidal film of the present disclosure significantly improves the bactericidal effect of the protective mask and is thus of high practical value.

The above description is merely preferred embodiments of the present invention, which cannot be viewed as a limitation of the claims. Any equivalent modifications of the structure or process described in the specification of the present disclosure shall fall into the scope of the present disclosure.

What is claimed is:

1. A method for preparing a bactericidal film on fiber cloth, comprising:
    (a) Preprocessing by cleansing a reel of fiber cloth and blow-drying the reel;
    (b) Vacuum processing by placing the reel of fiber cloth into a vacuum chamber, and vacuuming the chamber to 1×10-3 Pa;
    (c) Coating a bactericidal film layer by supplying a DC power and a mid-frequency power to a plurality of sputtering targets, regulating the voltage to 600-1000V and 30-40V respectively, wherein the duty ratio of the mid-frequency power is 20-30%; introducing argon gas to increase the chamber pressure to 0.3 Pa; wherein the plurality of sputtering targets, comprising a silicon sputtering target, silicon carbide sputtering targets and silver sputtering targets, are initiated; subsequently, initiating the reel of fiber cloth, wherein the reel of fiber cloth is advanced at a linear speed of 0.1-0.3 m/s, wherein the current densities of the silicon target and each of the silicon carbide sputtering targets are 4-6 A, and wherein the current density of each of the silver sputtering targets is 0.3-0.6 A; regulating the chamber temperature to 10-20° C.; wherein in the advancing direction of the fiber cloth, the plurality of sputtering targets are positioned in the following order: a silicon target, a silicon carbide target, a silver target, a silicon carbide target, a silver target, a silicon carbide target and a silver target, and then sputtering all of the plurality of targets simultaneously to form a multi-layer of a bactericidal film layer of silicon carbide and silver on the surface of the fiber cloth; wherein the silicon forms a bonding layer between the bactericidal film and the substrate;
    (d) Completing the film coating by stopping the silicon targets, the silicon carbide targets and the silver targets first, and then turning off the argon gas; letting the chamber cool by waiting for 5-10 minutes; injecting air into the chamber intermittently until the pressure in the chamber and the atmospheric pressure are balanced.

2. The method for preparing a bactericidal film on fiber cloth of claim 1, wherein the reel of fiber cloth is cleaned by absorbing and removing the dust and gas off the cloth surface, and wherein the blow-drying temperature does not exceed a temperature of 60° C.

3. The method for preparing a bactericidal film on fiber cloth of claim 1, wherein the flow rate of argon gas is 100-250 sccm, and the coating duration is 10-60 seconds.

* * * * *